United States Patent [19]
Matson

[11] Patent Number: 5,290,420
[45] Date of Patent: Mar. 1, 1994

[54] SAMPLING SYSTEM AND ANALYSIS CELL FOR STRIPPING VOLTAMMETRY

[75] Inventor: Wayne R. Matson, Ayer, Mass.

[73] Assignee: ESA, Inc., Bedford, Mass.

[21] Appl. No.: 929,702

[22] Filed: Aug. 12, 1992

[51] Int. Cl.⁵ .......................................... G01N 27/26
[52] U.S. Cl. ................................. 204/403; 204/409; 204/412; 204/416; 204/418; 204/419; 204/153.12
[58] Field of Search ............... 204/403, 405, 409, 412, 204/416, 418, 419, 433, 434, 435, 413, 153.12

[56] References Cited

U.S. PATENT DOCUMENTS

| | | | |
|---|---|---|---|
| 4,090,926 | 5/1978 | Matson | 204/413 |
| 4,214,968 | 7/1980 | Battaglia et al. | 204/418 |
| 5,046,496 | 9/1991 | Betts et al. | 204/403 |
| 5,120,420 | 6/1992 | Nankai et al. | 204/403 |
| 5,141,868 | 8/1992 | Shanks et al. | 204/403 |

Primary Examiner—John Niebling
Assistant Examiner—Bruce F. Bell
Attorney, Agent, or Firm—Hayes, Soloway, Hennessey & Hage

[57] ABSTRACT

A combination sampling/electrochemical analysis cell comprises an enclosure having a hollow therein, at least one inlet leading to the hollow, a vent leading from the hollow, at least one testing electrode, at least one counter electrode, and at least one reference electrode, all disposed at least in part in the hollow. A testing reagent is also contained in the hollow.

29 Claims, 3 Drawing Sheets

SAMPLING SYSTEM AND ANALYSIS CELL FOR STRIPPING VOLTAMMETRY

BACKGROUND OF THE INVENTION

The present invention relates to electrochemical analysis, and more particularly to an integrated sampling system incorporating electrochemical sensors and reagents. The invention has particular utility in connection with testing lead levels in human blood and will be described in connection with such utility, although other utilities are contemplated.

It has long been possible to test both qualitatively and quantitatively for ionic materials in an aqueous sample by electrolytic means, and to record the electrical potential of deposition of the ions on an electrode. In one form of such testing known as stripping voltammetry, the ions are first deposited on an electrode and thereafter the potential is varied to strip the deposited material from the electrode and redissolve it in the sample liquid. This operation is known as stripping voltammetry and since it is ordinarily used by plating cathodically and stripping anodically to detect and measure metallic ions, it is often known as anodic stripping voltammetry. By means of anodic stripping voltammetry, it has been found possible to perform relatively quickly simple and accurate tests to measure minute traces of materials, for example, to test for the presence of informative or dangerous impurities in the human bloodstream. As a result anodic stripping voltammetry systems such as available from ESA, Inc., the assignee of the subject application, have achieved widespread field and laboratory use since at least about 1975.

The application of stripping voltammetry to testing for impurities in the human blood stream, improved electrochemical detection systems, cells, reagents and processes are the subject of several of my prior U.S. Patents, including U.S. Pat. Nos. 3,855,099, 4,201,646, 4,090,926, 4,374,041 and 4,233,031, and U.S. Reissue Pat. No. 32,920, the disclosures of which are incorporated by reference.

While anodic stripping voltammetry systems provide satisfactory results for the general population, recent studies have shown problems of individual variability affecting low blood level value (5 μg %) accuracy on commercial exchange reagents/anodic stripping voltammetry systems.

Lead in a whole blood sample is distributed in a number of different compartments with a high degree of individual variable in binding constants and kinetics. Similarly, individual variability in copper levels and other endogenous oxidizable/reducible compounds can affect the envelope of the electroanalytical curve and hence the analytical value for lead.

Simplistically, generally 97-99% of lead is bound to the erythrocyte. However, within the erythrocyte there appear to be compartments both on the external surface of the cells and within the cell and sites with varying levels of binding constants. Thus, there is a level of lead typically between 2-10 μg % that will not release into EDTA; a level (typically 2-8 μg %) that will not release into acid; and a level (typically 0.2-2 μg %) that will not release into commercial exchange reagents such as Metexchange ® available from ESA, Inc. The reasons for the variability across a range of individuals is not clear, although in the specific disorder, sickle cell trait, it has been suggested that sickle cells are resistant to rupture and release and that in other cases a high concentration of Fetal Hemoglobin may imply a higher binding constant.

When lead is released from the erythrocyte to a solution matrix of whole blood residue and exchange reagents, it is bound secondarily in a number of labile ligands (sulfhydryls, phospholipids, amino acids, peptides) which in the aggregate change its apparent diffusion constant from $6.9 \times 10^{-6}$ cm$^2$/sec to approximately $7.8 \times 10^{-6}$ cm$^2$/sec in a 30:1 dilution to approximately $8 \times 10^{-7}$ cm$^2$/sec in whole blood with added solid exchanger.

The analytical implications of these observations are that any technique employing direct blood measurement, such as electrochemistry or enzyme coupling, must be designed to handle the extremes of individual variability, and that it is relatively easy to be fooled into assuming technical adequacy by evaluating a technique on pools or artificially spiked samples.

The approach taken in commercial reagent/anodic stripping voltammetry to addressing the problems of lead distribution has been to dilute the blood sample, for example, by 30 times, and to provide the strongest exchange reagent possible consistent with long term sensor operation, and to operate the sensor at 1.5-1.7 half times (1 minute) to significantly reduce the lead level in solution and thus compensate for differing ligand formation constants. Essentially, the approach is a compromise among sensor longevity, sensitivity, accuracy and analysis time.

Other problems in the prior art include sample contamination, for example, due to smearing during blood drawing and sample mislabeling or mixup.

OBJECT OF THE INVENTION

It is therefore an object of the present invention to provide an improved electrochemical analytical system which overcomes the aforesaid and other problems of the prior art. A more specific object of the present invention is to provide an electrochemical analytical system which permits the incorporation of more aggressive exchange reagents without reducing sensor life. Yet another object of the present invention is to provide an electrochemical detection system which permits assay of blood without dilution.

Other objects of the invention will in part appear obvious and will in part appear hereinafter. The invention accordingly comprises the apparatus possessing the construction, combination of elements and arrangement of parts, the process comprising the several steps in relation of one or more steps with respect to the others, and the compositions comprising the several materials, all of which will be exemplified in the following detailed description and scope of application as will be indicated in the claims.

BRIEF DESCRIPTION OF THE PRESENT INVENTION

The present invention provides a disposable integrated sampling/electrochemical analysis cell incorporating one or more testing electrodes and selected exchange reagents directly in the cell. In a presently preferred embodiment of the invention, the cell comprises a capillary inlet to a hollow containing one or a plurality of testing and counter electrodes, and at least one reference electrode. An electrochemical reagent selected for the particular electrochemical test, in dry or high viscosity form is deposited in the hollow, preferably on the testing electrode. Completing the cell are means for connecting the testing, counter and reference electrodes to selected electrical potentials. The integrated sampling/analysis cell preferably incorporates or is designed to mate with a capillary finger stick or the like for drawing blood, and is formed of a material which allows for capillary action take-up of the sample (e.g. blood) to be tested.

BRIEF DESCRIPTION OF THE DRAWINGS

A fuller understanding of the nature and objects of the present invention will be had by reference to the following detailed description taken in combination with the accompanying drawings, wherein like numerals depict like parts, and wherein.

The present invention provides an integrated sampling/analysis cell particularly adapted for microblood sampling and analysis by stripping voltammetry. As applied to identifying heavy metal contaminants, trace mineral components or trace elements in samples of human blood, the integrated sampling/analysis system also includes a reagent for preconditioning the blood sample for electrochemical analysis.

Figure 1:
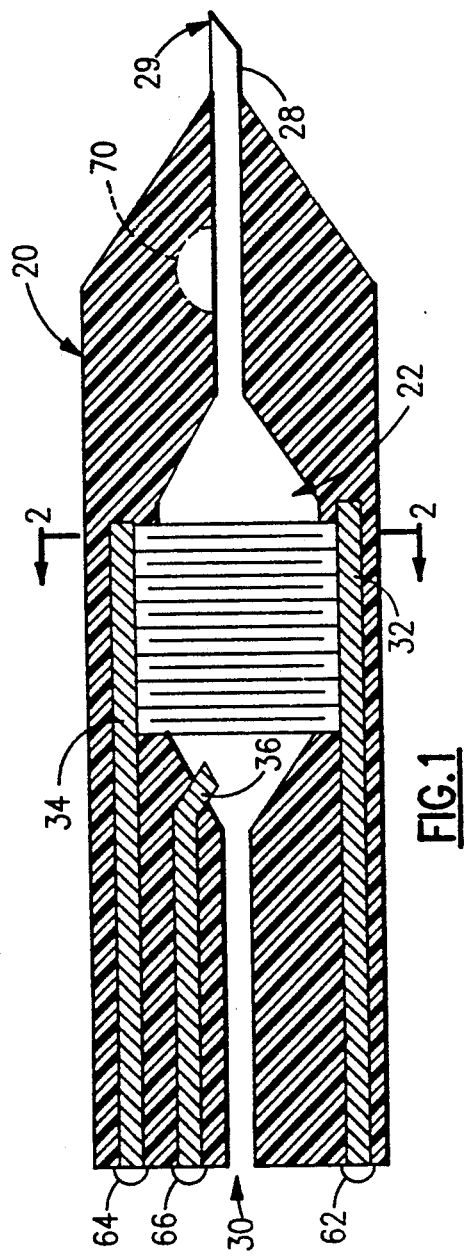
FIG. 1 is a plan view, in cross section, of an integrated sampling electrochemical analysis cell in accordance with the present invention.
Figure 2:
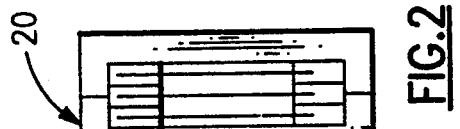
FIG. 2 is a side elevational view, in cross section, of the integrated sampling/electrochemical analysis cell of FIG. 1 taken along line 2—2.
Figure 3:
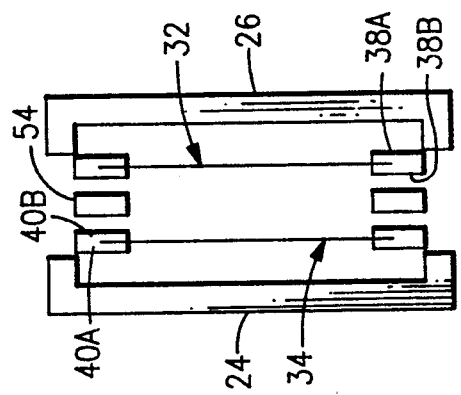
FIG. 3 is a view, similar to FIG. 2, in exploded form.
Figure 4:
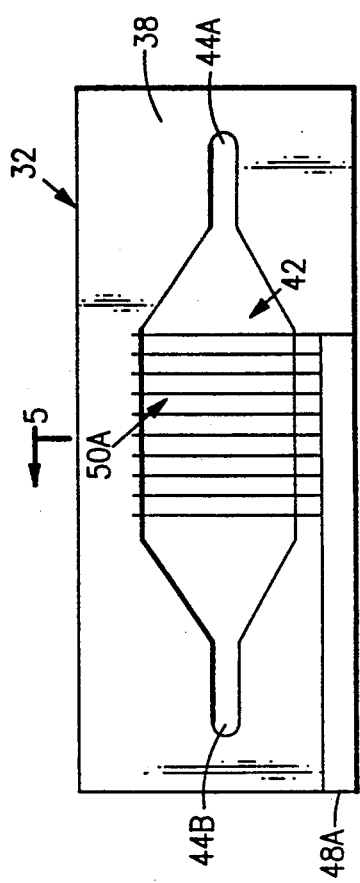
FIG. 4 is a plan view of a testing electrode element portion of the integrated sampling/electrochemical analysis cell of FIG. 1.
Figure 5:
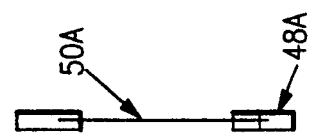
FIG. 5 is a side view of the testing electrode element portion of FIG. 4 taken along line 5—5.
Figure 7:
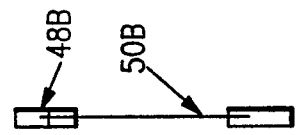
FIG. 7 is a cross-sectional view of the counter electrode element portion shown in FIG. 6, taken along line 7—7.
Figure 6:
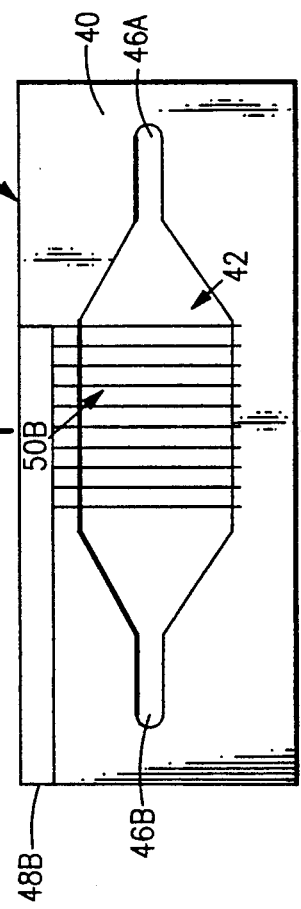
FIG. 6 is a view similar to FIG. 4 of a counter electrode element of the integrated sampling/electrochemical analysis cell of FIG. 1.

Referring in particular to FIGS. 1-3 of the drawings, the integrated sampling/analysis cell in preferred form comprises a hollow liquid-tight enclosure indicated generally at 20 and defining internal chamber 22. Enclosure 20 comprises a two-piece "clam-shell" 24 and 26, and includes an extended inlet tube 28 terminating in a sharpened bevel at 29, and a vent 30 both communicating with chamber 22. Inlet tube 28 is sized to permit capillary action of the material being sampled, for example, blood. Thus, in the case of human blood sampling, inlet tube 28 should have a cross-sectional dimension less than or equal to about 0.7 centimeters. Vent 30 may be the same size as inlet tube 28, or may be a different size and cross-section. Inlet tube 28 and vent 30 may comprise a variety of cross-sections, but preferably are round or rectangular in cross-section.

Referring also to FIGS. 4-7, the integrated sampling/analysis cell in accordance with the present invention includes at least one testing electrode 32, at least one counter electrode 34 and at least one reference electrode 36. Testing electrode 32 and counter electrode 34 may comprise screened or printed electrodes, but preferably comprise transverse arrays of graphite or carbon fiber electrode elements 50A and 50B affixed to one or sandwiched between a pair of sheets 38A, 38B and 40A, 40B of plastic material such as polyethylene. In the latter case each sheet 38A and 38B and 40A and 40B should have a cutout area comprising a main cutout area 42 which collectively define chamber 22, and blind cutout ends 44A and 44B and 46A and 46B which are in fluid communication with inlet tube 28 and vent 30, respectively. A contact bus 48A and 48B such as silver foil or the like is affixed along one edge of one of sheets 38A and 38B and 40A and 40B, respectively, underlying or overlying edges of the carbon or graphite fiber electrode elements 50A and 50B, respectively, in electrical contact therewith.

Carbon or graphite fiber electrode elements 50A and 50B, respectively, preferably comprise 8 micron carbon fibers spaced from 700 to 7,000 fibers per inch. Such carbon fibers are available in carded fiber rolls from Stack Pole Fibers of Lowell, Mass. and Fiber Materials, Inc. of Brunswick, Me. However, the invention is not so limited to use of such commercially available carbon fiber materials.

Completing the integrated sampling/analysis cell are apertured spacers 54, similar in plan to sheets 38A and 38B and 40A and 40B for spacing the testing and counter electrodes from one another, and for increasing the cell working volume.

As seen particularly in FIG. 2, sheets 38A and 38B and 40A and 40B and spacers 54 preferably are slightly smaller in plan than clam shells 24 and 26 so as to fit entirely within the clam shells 24 and 26 when the latter are assembled together.

A feature and advantage of the present invention is to provide an integrated sampling/analysis cell which is relatively inexpensive to manufacture and may be used with micro-capillary sampling techniques. Accordingly, enclosure 20, clam shells 24 and 26, sheets 38A, 38B and 40A, 40B and spacers 54 should be made of materials which are electrochemically insulating, and inert to the materials being sampled and to the reagents employed as will be described in detail hereinafter. Clam shells 24, 26, sheets 38A, 38B, 40A and 40B, and spacers 54 also should be formed of a material capable of allowing capillary action of the material being sampled, e.g. blood. Also, in order to permit assembly of the integrated sampling/analysis cell, for example, by heat sealing or ultrasonic welding, clam shells 24 and 26 should be formed of a thermal plastic material. Thus, the preferred materials to clam shells 24 and 26 are polycarbonate or the like, while sheets 38A, 38B, 40A and 40B and spacers 54 preferably are made of polyvinyl chloride, polycarbonate or polypropylene.

Another feature and advantage of the present invention is the incorporation of a reagent into the integrated sampling/analysis cell. For example, in the case of testing for lead in human blood samples, a reagent should be included for releasing iron from serum. Conventional aqueous based exchange reagents are of limited utility due to possibility that the reagent may drain from the cell during storage, or may be driven or displaced from the cell by the capillary action takeup of the blood sample. Accordingly, exchange reagents particularly useful in the integrated sampling/analysis cell of the present invention should be capable of being dried-in-place in the cell, preferably on or adjacent the testing electrodes, or of sufficient viscosity to resist loss by drainage or displacement. Preferred reagents include mixtures of one or more acids, preferably organic acids, with one or more salts, preferably of alkali metal salts or rare earth divalent or trivalent cations. Preferred are mixtures of monochloro acetic acid with one or more of $LaCl_3$, $AlCl_3$, $CrCl_3$, $CaCl_2$ and $HgCl_2$. Particularly preferred are the following

| REAGENT A: | |
|---|---|
| Monochloro acetic acid | 0.1M |
| $LaCl_3$ | 0.5M |
| REAGENT B: | |
| Monochloro acetic acid | 0.1M |
| $LaCl_3$ | 0.5M |
| $AlCl_3$ | 0.2M |
| Triton X-100[1] | 4% |
| REAGENT C: | Weight Ratio |
| Monochloro acetic acid | 3 |
| $CrCl_3$ | 10 |
| $AlCl_3$ | 5 |
| $LaCl_3$ | 10 |
| $CaCl_2$ | 2 |
| $HgCl_2$ | 1 |
| Triton X-100 | 5 |

[1] Triton X-100 is a polyalcohol surfactant available from Sigma Chmicals, and is known for use as a blood lysing agent. Other blood lysing surfactants are available commercially and may also advantageously be used in accordance with the present invention.

The reagent typically is employed in a volume amount equivalent to at most 0.5-5%, typically about 1% of the cell working volume.

While reagents such as above listed are considered to be too aggressive for use in connection with conventional anodic stripping electrode sensors and typically will destroy a conventional sensor in a matter of a few weeks, such reagents advantageously may be used in connection with one-time-use integrated sampling-/analytical testing cells in accordance with the present invention, and provide improved exchange efficiencies as compared with conventional exchange materials.

Construction of the integrated sampling and analysis cell made in accordance with the present invention is straightforward. The clam shell halves 24, 26 may be formed, for example, by molding, and sheets 38A, 38B, 40A and 40B, and spacers 54 are formed by stamping. The electrode bus bars 48A, 48B are then deposited on sheets 38A, 38B, 40A and 40B, for example, by screen printing. The reference electrode 36 may be similarly deposited on one of the clam shells 24, 26. Carded carbon fiber electrode elements 50A and 50B are then laid in spaced position between sheets 38A and 38B, and 40A and 40B, respectively, with one end thereof in contact with bus bars 48A, 48B, and the sheets are fixed together by means of adhesive whereby to capture the carbon fibers therebetween, and form the counter and testing electrodes. The testing electrode is then treated with a measured quantity of reagent, and the reagent is dried-in-place. The counter and testing electrodes are then assembled in a stack with spacers 54 therebetween and the stack is loaded into one of the one-half clam shells. The other half of the clam shell is then assembled to the first half, and the clam shell halves are fixed together, for example, as by thermal welding.

In a particularly preferred embodiment of the invention, the integrated sampling/analytical cell comprises two test electrode arrays, and one counter electrode array of 8μ carbon fibers, spaced at about 1000 fibers per inch, and the cell has a working volume of less than about 100 μl. For example, the cell may have approximate internal dimensions of about 0.05 cm × 0.5 cm × 2.5 cm, giving an overall working volume of about 63 μl.

A feature and advantage of the present invention is that the blood is subjected to analysis directly, i.e. without dilution as in the case of conventional anodic stripping techniques. This provides a 30:1 concentration enhancement which in turn results in enhanced sensitivity notwithstanding a decreased diffusion constant because of lower sample volume as compared with conventional anodic stripping techniques.

Figure 8:
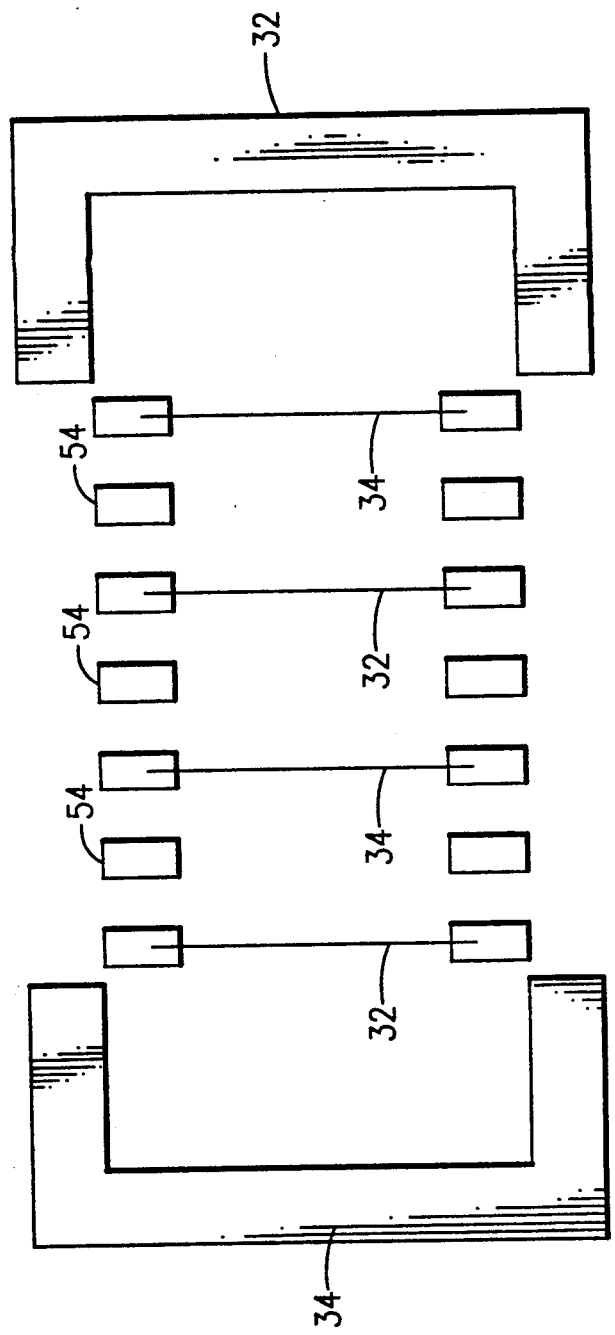
FIG. 8 is an exploded view, similar to FIG. 3 of an alternative form of integrated sampling/electrochemical analysis cell made in accordance with the present invention.

The invention is susceptible to modification. For example, as shown in FIG. 8, the integrated sampling-/analytical cell may comprise a stack of a plurality of testing and counter electrodes 32 and 34, respectively. Employing a plurality of testing and counter electrodes may increase analytical accuracy and/or reduce response time.

Completing the integrated sampling/analytical cell in accordance with the present invention comprise contact means 62 such as contact pads for electrically connecting the testing electrode to a testing potential; contact means 64 for connecting the counter electrode or counter electrodes to a counter potential; and contact means 66 for connecting the reference electrode to a reference potential, all in accordance with the teachings of my previous U.S. patents as above mentioned.

The integrated sampling/analytical testing cell in accordance with the present invention has a number of advantages over prior art sampling and analysis techniques. For one, the volume of the blood assay is defined by the internal geometry of the sampling/analytical testing cell and thus is independent of the volume drawn as long as the testing electrode is covered. This eliminates possible test inaccuracies, and eliminates the need to locate a patient in the event sufficient blood was not drawn in the initial sampling. Also, direct anodic stripping whole blood in accordance with the present invention has the effect of shifting the stripping peak 30-50 mv for the cathodic to copper, presumably because of the thirty-fold higher concentration of lead binding labile ligands. This effectively eliminates the effect of copper on the stripping curve envelope. And, an additional effect of reducing the variation in the envelope is the quiescent reduction of blood oxygen and other reducible blood moieties as compared with conventional anodic stripping techniques which may reintroduce oxygen, etc. through stirring. These two effects result in an underlying or blank envelope that requires compensation for curvature in the lead peak zone of less than about 0.5 microgram percent versus the current compensation of 8-12 microgram percent. Yet another feature and advantage of the present invention and which results from reduced cell/volume sensor area is that half times also are reduced.

Another feature and advantage of the present invention is that the electrode fibers which are oriented transverse to the test solution draw appear to prevent the draw of air, and thus bubbles, in the cell working volume under normal conditions. Alternatively, a small expansion volume shown in phantom at 70 in FIG. 1 may be provided in the inlet tube 28.

While the present invention has been described in connection with the sampling and analysis of testing lead levels in blood, it will be appreciated that the integrated sampling/analysis cells in accordance with the present invention may be employed in connection with a sampling and analysis of blood for a variety of metals, including cadmium, copper, zinc, thallium, silver, gold, bismuth and the like. Moreover, the integrated sampling/analysis cell in accordance with the present invention may be used for sampling and analysis of other bodily fluids such as urine, saliva, perspiration, tears, etc., or non-bodily fluids such as gasoline, water, etc. In such case, inlet tube 28 may be sized, for example, for injection of fluids to be tested. In such case, inlet tube 28 may include a rubber stopper or the like.

I claim:

1. A disposable combination capillary sampling/electrochemical analysis cell comprising an enclosure having a hollow therein, at least one capillary inlet leading to said hollow wherein said inlet permits uptake of the material being sampled, a vent leading from said hollow, at least one testing electrode, at least one counter electrode, and at least one reference electrode, all disposed in part in said hollow, said hollow further including a testing reagent.

2. A cell according to claim 1, wherein said testing reagent is deposited at least in part in contact with said testing electrode.

3. A cell according to claim 1, wherein said testing reagent is dried in place on said testing electrode.

4. A cell according to claim 3, wherein said testing reagent comprises a mixture of an acid and one or more salts.

5. A cell according to claim 4, wherein said salt is selected from the group consisting of an alkali metal, salt, a rare earth divalent cation, a rare earth trivalent cation, and mixtures thereof.

6. A cell according to claim 5, wherein said alkali salt is selected from the group consisting of $LaCl_3$, $AlCl_3$, $CrCl_3$, $CaCl_2$, $HgCl_2$, and mixtures thereof.

7. A cell according to claim 4, wherein said acid comprises an organic acid.

8. A cell according to claim 7, wherein said organic acid comprises monochloro acetic acid.

9. A cell according to claim 1, wherein said reagent also comprises a surfactant.

10. A cell according to claim 1, wherein said at least one testing electrode comprises a plurality of spaced carbon or graphite fibers electrically connected to a common bus.

11. A cell according to claim 10, wherein said carbon or graphite fibers are disposed generally transverse to the inlet.

12. A cell according to claim 1, and further comprising an expansion area in said inlet.

13. A cell according to claim 1, having a working volume of less than about 100 $\mu$l.

14. A capillary sampling cell incorporating at least one testing electrode, at least one counterelectrode, at least one reference electrode, a testing reagent in the cell, and a capillary inlet which permits uptake of the material being sampled.

15. A cell according to claim 14, wherein said testing reagent is deposited at least in part in contact with said testing electrode.

16. A cell according to claim 14, wherein said testing reagent is dried in place on said testing electrode.

17. A cell according to claim 14, wherein said testing reagent comprises a mixture of an acid and one or more salts.

18. A cell according to claim 17, wherein said salt is selected from the group consisting of an alkali metal, salt, a rare earth divalent cation, a rare earth trivalent cation, and mixtures thereof.

19. A cell according to claim 18, wherein said alkali salt is selected from the group consisting of $LaCl_3$, $AlCl_3$, $CrCl_3$, $CaCl_2$, $HgCl_2$, and mixtures thereof.

20. A cell according to claim 17, wherein said acid comprises an organic acid.

21. A cell according to claim 20, wherein said organic acid comprises monochloro acetic acid.

22. A cell according to claim 14, wherein said reagent also comprises a surfactant.

23. A cell according to claim 14, wherein said at least one testing electrode comprises a plurality of spaced carbon or graphite fibers electrically connected to a common bus.

24. A cell according to claim 23, wherein said carbon or graphite fibers are disposed generally transverse to the inlet.

25. A cell according to claim 14, having a working volume of less than about 100 $\mu$l.

26. A cell according to claim 1, wherein said cell includes a reagent for treating a human blood sample preparatory to electrically detecting and measuring lead content of said sample, wherein said reagent comprises a mixture of an organic acid and a salt selected from the group consisting of $LaCl_3$, $AlCl_3$, $CrCl_3$, $CaCl_2$, $HgCl_2$ and mixtures thereof.

27. A reagent according to claim 26, wherein said organic acid comprises monochloro acetic acid.

28. A cell according to claim 1, wherein said inlet terminates in a sharpened bevel.

29. A cell according to claim 14, wherein said cell includes an inlet tube sharpened at its distal end.

* * * * *